US010653564B2

(12) United States Patent
Yamaguchi et al.

(10) Patent No.: US 10,653,564 B2
(45) Date of Patent: May 19, 2020

(54) METHOD FOR MANUFACTURE OF ABSORBENT ARTICLE

(71) Applicant: UNICHARM CORPORATION, Ehime (JP)

(72) Inventors: Masashi Yamaguchi, Kagawa (JP); Hiroki Goda, Kagawa (JP); Atsushi Tsukuda, Kagawa (JP); Hiroaki Tada, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 139 days.

(21) Appl. No.: 16/068,363

(22) PCT Filed: Nov. 22, 2016

(86) PCT No.: PCT/JP2016/084668
§ 371 (c)(1),
(2) Date: Jul. 6, 2018

(87) PCT Pub. No.: WO2017/119204
PCT Pub. Date: Jul. 13, 2017

(65) Prior Publication Data
US 2019/0015262 A1    Jan. 17, 2019

(30) Foreign Application Priority Data

Jan. 8, 2016 (JP) ................................. 2016-002929

(51) Int. Cl.
*A61F 13/15* (2006.01)
*A61F 13/84* (2006.01)
(Continued)

(52) U.S. Cl.
CPC ........ *A61F 13/15593* (2013.01); *A61F 13/15* (2013.01); *A61F 13/1565* (2013.01);
(Continued)

(58) Field of Classification Search
None
See application file for complete search history.

(56) References Cited

U.S. PATENT DOCUMENTS 5,897,541 A      4/1999 Uitenbroek et al.
2007/0087169 A1  4/2007 McFall
(Continued)

FOREIGN PATENT DOCUMENTS

JP    S63-64709 U    4/1988
JP    H10-506586 A   6/1988
(Continued)

*Primary Examiner* — Jeffry H Aftergut
(74) *Attorney, Agent, or Firm* — Hauptman Ham, LLP

(57) ABSTRACT

The purpose of the present invention is to provide a method for manufacture of an absorbent article, with which it is possible to form a desired coloring pattern upon an absorbent article and to reliably manage the quality of said coloring pattern. Provided is a method for manufacture of an absorbent article, in which: microcapsules, which are provided upon a substrate and in which coloring agents are enclosed, are destroyed in a prescribed pattern, and the coloring agents discharged upon the substrate; and the substrate is coated with a developer, causing the coloring to be expressed in the prescribed pattern via a reaction between the coloring agents and the developer.

12 Claims, 5 Drawing Sheets

(51) Int. Cl.
*A61F 13/533* (2006.01)
*A61F 13/53* (2006.01)
A61F 13/531 (2006.01)
A61F 13/539 (2006.01)
B32B 27/20 (2006.01)
D01F 1/04 (2006.01)

(52) U.S. Cl.
CPC ............ *A61F 13/53* (2013.01); *A61F 13/533* (2013.01); *A61F 13/84* (2013.01); *A61F 13/15203* (2013.01); *A61F 2013/15869* (2013.01); *A61F 2013/15934* (2013.01); *A61F 2013/5315* (2013.01); *A61F 2013/53991* (2013.01); *A61F 2013/8497* (2013.01); *B32B 27/20* (2013.01); *D01F 1/04* (2013.01)

(56) References Cited

U.S. PATENT DOCUMENTS

2008/0269704 A1* 10/2008 Hansson ............ A61F 13/15772
604/366
2011/0274834 A1 11/2011 Brown et al.

FOREIGN PATENT DOCUMENTS

| JP | H4-8582 A | 1/1992 |
| JP | 2002-102021 A | 4/2002 |
| JP | 2007-132756 A | 5/2007 |
| JP | 2008-212931 A | 9/2008 |
| JP | 2010-173087 A | 8/2010 |
| JP | 4787991 B2 | 10/2011 |

* cited by examiner

METHOD FOR MANUFACTURE OF ABSORBENT ARTICLE

FIELD

The present invention relates to a method for manufacturing an absorbent article, and more specifically it relates to a method for manufacturing an absorbent article comprising a step of forming a colored pattern using coloring agent microcapsules and a developer in a base material of an absorbent article.

BACKGROUND

In manufacturing steps for absorbent articles such as diapers, in order to improve the visual effect of joining patterns for the purpose of decoration as well as process and quality control, it has been proposed to apply thermochromic colorants or pressure-sensitive microcapsules and create coloration at patterns of joining between absorbent article members by heat or pressure applied during the joining process (Patent Literature 1: Japanese Patent Publication No. 4787991).

CITATION LIST

Patent Literature

[Patent Literature 1] Japanese Patent Publication No. 4787991

SUMMARY

Technical Problem

In the method of Patent Literature 1, the joining pattern has a coloring property that is developed by heat and/or pressure applied during joining, the joining being carried out by embossing, laser welding, thermal bonding, adhesive connection or the like. In the method of Patent Literature 1, however, the coloring components that have gradually adhered to the pattern rolls become transferred onto the base material during continuous operation, leading to a problem as it becomes difficult to stably manage the quality of the colored pattern. Moreover, applying of the microencapsulated coloring agent and developer is before the joining step, and the chemical agents for the coloring agent and developer are generally used in the form of aqueous dispersions. From the viewpoint of dispersibility and applying properties it is not preferred for the solid concentration of the aqueous dispersion to be too high, but in the method of Patent Literature 1, when the necessary amount of chemical agents used for coloring are applied onto an absorbent body or the like and a large amount of water is added to the base material, this leads to problems with the product, such as a tendency for pressure application by the pattern roll to causes the absorbent body to become hard, or problems that arise during continuous manufacturing, such as a tendency for the base material to cling onto and wrap around the pattern roll.

It is therefore an object of the present invention to provide a method for manufacturing an absorbent article wherein a desired colored pattern can be formed in the absorbent article and its quality can be stably managed.

Solution to Problem

In order to achieve the object stated above, the present invention provides, according to aspect 1,
a method for manufacturing an absorbent article having a base material, the method comprising:
a first step for providing a base material having microcapsules confining a coloring agent,
a second step for breaking the microcapsules in a prescribed pattern in the base material to release the coloring agent into the base material in the prescribed pattern, and
a third step for applying a developer onto the base material in which the coloring agent has been released in the prescribed pattern, so that the coloring agent and the developer are reacted to effect coloring (to develop a color) in at least a portion of the prescribed pattern.

According to aspect 1, since the first and second steps in which the microcapsules confining a coloring agent (hereunder also referred to as "coloring agent microcapsules") in the base material are broken to release the coloring agent in the prescribed pattern and the third step in which the released coloring agent and the developer are reacted to effect coloring (or develop a color) are different steps than the third step, the developer may be applied over only a portion of the pattern of the coloring agent that has been released in the first and second steps, instead of over its entirety, in order to effect coloring (to develop a color). Furthermore, if the coloring agent used is a coloring agent that is colorless before reaction with the developer, then the manufacturing equipment and tools will not suffer color contamination, and the same coloring roll can therefore be used for both colored embossing and colorless embossing.

Moreover, according to aspect 1, since only the coloring agent microcapsules are applied in the first step, without applying the developer, it is possible to reduce the amount of water in the applying solution used in the first step, compared to Patent Literature 1 wherein the coloring agent microcapsules and the developer are simultaneously applied in the first step. While the amount of water can be reduced by increasing the concentration of the coloring agent microcapsules or developer in the applying solution, this is not always a desirable situation for applying, and there is also a limit to this strategy. When the base material is an absorbent body or the like, and the base material contains a large amount of water, there is a risk of problems occurring during the process of applying pressure, vibration or heat using a pattern roll or similar means in the second step, such problems including hardening of the base material or wrapping around the pattern roll, but according to the invention this risk can be reduced.

The present invention also includes the following aspects.
(Aspect 2)
The method according to aspect 1, wherein in the second step, the microcapsules are broken by applying at least one selected from among pressure, heat and vibration.

According to aspect 2, the method of breaking the coloring agent microcapsules may be selected from among pressure, heat and vibration, and therefore wider freedom of selection is possible in the manufacturing process.
(Aspect 3)
The method according to aspect 1 or 2, wherein in the second step, the microcapsules are broken in the prescribed pattern by embossing, and in the third step, the coloring is effected (the color is developed) in at least a portion of the prescribed pattern.

According to aspect 3, since embossing is generally carried out for absorbent articles, and they include patterns that determine the quality of the absorbent articles, if color development in the embossed pattern is possible, quality control during the manufacturing process can be carried out in a stable manner manufacturing, while also allowing the quality of the absorbent article to be easily recognized, thus also enhancing the high quality feel of the product.

(Aspect 4)

The method according to any one of aspects 1 to 3, wherein the base material comprises an absorbent body.

According to aspect 4, coloring is made in a prescribed pattern in the absorbent body, which is the main member of the absorbent article, thereby allowing quality control to be carried out in a stable manner during the manufacturing process, while also allowing the quality of the absorbent body, as the main member of the absorbent article, to be easily recognized, thus also enhancing the high quality feel of the product.

(Aspect 5)

The method according to aspect 4, wherein the absorbent body comprises an absorbent core between an upper wrap sheet and a lower wrap sheet, and in the first step, the microcapsules are supplied to the upper wrap sheet and/or and the lower wrap sheet, while in the third step, the coloring is effected in the upper wrap sheet and/or the lower wrap sheet.

According to aspect 5, a coloring pattern is present on the surface of the absorbent body, making it easy to see, and since the coloring pattern is present on the absorbent body, the feel during use of the absorbent article and its high quality feel are enhanced.

(Aspect 6)

The method according to aspect 5, wherein in the first step the microcapsules are supplied to the upper wrap sheet, in the second step squeeze grooves are formed in the absorbent body extending in the depthwise direction from the upper wrap sheet to the absorbent core and the lower wrap sheet, and in the third step the coloring is effected as a pattern of the squeeze grooves in the upper wrap sheet.

According to aspect 6, the pattern of squeeze grooves extending in the depthwise direction from the upper wrap sheet to the absorbent core and lower wrap sheet of the absorbent body consists of the sites of the flexion base points of the absorbent body, and therefore the pattern of squeeze grooves are a coloring pattern, and the feel during use and high quality feel of the product are enhanced.

(Aspect 7)

The method according to any one of aspects 4 to 6, wherein the absorbent article has a multilayer structure additionally comprising a skin side sheet on the skin side of the absorbent body and/or a non-skin side sheet on the non-skin side, in the first step the microcapsules are supplied to the absorbent body, the skin side sheet and/or the non-skin side sheet, and in the third step the coloring is effected in the absorbent body, the skin side sheet and/or the non-skin side sheet.

According to aspect 7, a coloring pattern is present, and is therefore visible, on the surface of the absorbent body or the skin side sheet or non-skin side sheet above or below it, and because the coloring pattern is present on the absorbent body or on the skin side sheet or non-skin side sheet above or below it, the feel during use and high quality feel of the absorbent article are enhanced.

Third Embodiment

The method according to any one of aspects 1 to 7, wherein the absorbent article is a disposable diaper, and a plurality of microperforations are formed on the outer section around the waist of the disposable diaper, the pattern of the microperforations being colored in the third step.

According to aspect 8, the pattern of the plurality of microperforations provided on the outer section around the waist of the disposable diaper are colored, and therefore by being colored blue in particular, a sense of air permeability is created and the feel during use and high quality feel of the product are enhanced.

(Aspect 9)

The method according to any one of aspects 1 to 8, wherein the surface of the base material having the microcapsules is the surface on the same side as the side of the base material on which the developer is applied. Incidentally, according to aspects 5 and 6, the coloring agent microcapsules are applied onto the skin side of the upper wrap sheet and/or the non-skin side of the lower wrap sheet. According to aspect 7 as well, the coloring pattern may be formed on the upper wrap sheet and/or lower wrap sheet of the absorbent body, and the coloring agent microcapsules may be applied onto the skin side of the upper wrap sheet and/or the non-skin side of the lower wrap sheet.

According to aspect 9, the coloring agent microcapsules and developer are applied and applied onto the same surface of the base material, and it is therefore possible to facilitate production while also obtaining excellent coloring properties.

(Aspect 10)

The method according to any one of aspects 1 to 8, wherein the surface of the base material having the microcapsules is the surface on the opposite side from the side of the base material on which the developer is applied. Incidentally, according to aspects 5 and 6, the coloring agent microcapsules are applied onto the non-skin side of the upper wrap sheet and/or the skin side of the lower wrap sheet. According to aspect 7 as well, the coloring pattern may be formed on the upper wrap sheet of the absorbent body, and the coloring agent microcapsules may be applied onto the non-skin side of the upper wrap sheet and/or the skin side of the lower wrap sheet.

According to aspect 10, the coloring agent microcapsules are applied onto the surface of the opposite side from the side of the base material on which the developer is applied, and therefore when a roller, for example, is used in the step of breaking the coloring agent microcapsules, the risk of inadvertent breaking of the coloring agent microcapsules is reduced.

(Aspect 11)

The method according to any one of aspects 1 to 10, which further comprises a hot-melt joining step in which the base material is hot-melt joined to another structural member, and the first step is carried out after the hot-melt joining step.

According to aspect 11, microcapsules are applied and supplied onto the base material after the hot-melt joining step, so that there is no risk of breaking of the coloring agent microcapsules in the hot-melt joining step.

(Aspect 12)

The method according to any one of aspects 1 to 11, which further comprises a hot-melt joining step in which the base material is hot-melt joined to another structural member, the hot-melt joining step being after the first step but without breaking of the microcapsules in the hot-melt joining step.

According to aspect 12, a method is provided which allows coloration in a prescribed pattern such as embossing, without being affected by the heat of the hot-melt joining step.

Advantageous Effects of Invention

According to the invention there is provided a method for manufacturing an absorbent article wherein a desired colored pattern can be formed in the absorbent article and its quality can be stably managed.

DESCRIPTION OF EMBODIMENTS

Figure 1:
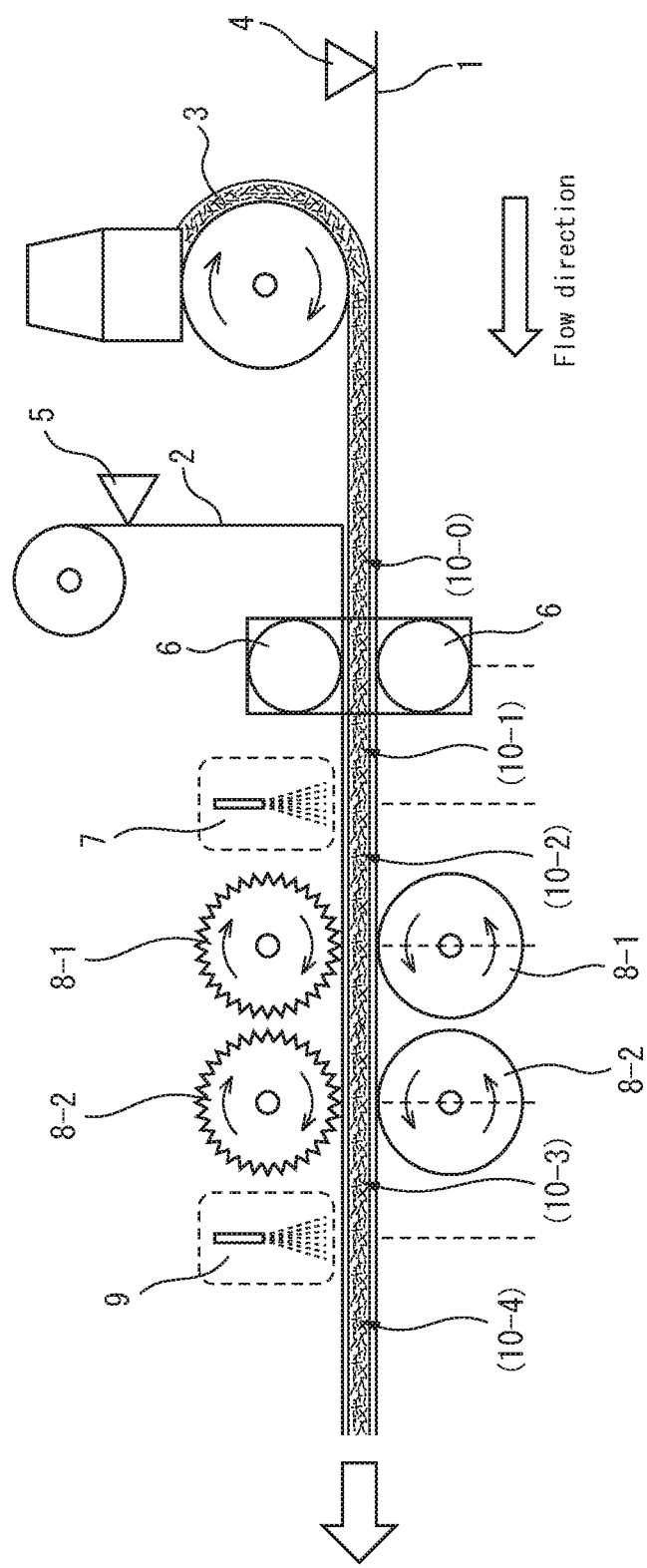
FIG. 1 is a diagram showing an example of a manufacturing process for an absorbent body of the invention.

The present invention is a method for manufacturing an absorbent article having a base material, the method comprising a first step for providing a base material having microcapsules confining a coloring agent, a second step for breaking the microcapsules in a prescribed pattern in the base material to release the coloring agent into the base material in the prescribed pattern, and a third step for applying a developer onto the base material in which the coloring agent has been released in the prescribed pattern, so that the coloring agent and the developer are reacted to effect coloring (or develop a color) in at least a portion of the prescribed pattern.

(Absorbent Article)

The present invention relates to method for manufacturing an absorbent article. An "absorbent article" according to the invention is a product such as a pants-type or tape-type disposable diaper, sanitary napkin, incontinence pad or the like that is disposed in contact with the skin of the wearer and is used to absorb and retain bodily exudates such as urine, feces and menstrual discharge.

The absorbent article has an absorbent body for the purpose of absorption. The absorbent body generally comprises natural or synthetic absorbent fibers such as pulp or rayon or a superabsorbent polymer, as the absorbent core, and it may also comprise other materials such as opened tow (long filaments). The absorbent core may be wrapped with a core wrap such as a tissue.

The absorbent body of the absorbent article is generally disposed between a liquid-permeable skin side sheet (top sheet) and a liquid-impermeable outer sheet (back sheet).

The absorbent article having an absorbent body disposed between a liquid-permeable skin side sheet and a liquid-impermeable outer sheet has a shape suited for the purpose of a disposable diaper, sanitary napkin, incontinence pad or the like, and also has various additional members, each of which are joined in a prescribed pattern and are well-known in detail, and the method of the invention applies to all such absorbent articles.

(Base Material)

According to the invention, the base material of the absorbent article may be any material that can be colored by a coloring agent and a developer, and this comprises natural and synthetic fiber nonwoven fabrics, woven fabrics and knitted fabrics, and foamed sheets, made of pulp, cotton, rayon, viscose, polyester and the like. Hydrophilic materials are preferred from the viewpoint of the dye-fixing property. The resin film used may be any one that has a fixing property for coloring agents, but the numerous types with low fixing properties for coloring agents are generally not suitable. These may be used alone or as composite sheets (laminates).

The form of the base material is preferably a sheet form such as a skin side sheet or non-skin side sheet, which may be a tissue, nonwoven fabric or the like for use as a core wrap (and which may also be laminated). It may also be an absorbent body having an absorbent core covered by a core wrap such as a tissue or nonwoven fabric, or a composite member including an absorbent body and a liquid-permeable skin side sheet and liquid-impermeable outer sheet. The structural members composing such composite members may be used alone or in combinations.

Representative examples of base materials for the absorbent article of the invention include the absorbent body that is described below with reference to the attached drawings, and especially its upper wrap sheet, as well as complexes comprising combinations of the absorbent body with a skin side sheet and outer sheet, either in their entirety or structural members thereof, or combinations including skin side sheets and outer sheets.

(Microcapsules)

According to the invention, microcapsules confining a coloring agent (coloring agent microcapsules) are used.

For the purpose of the invention, the coloring agent microcapsules are microparticles with sizes of about 1 to 200 μm and preferably about 3 to 20 μm, comprising a liquid or solid core substance (containing a coloring agent) covered with a film substance. The method for producing the microcapsules may be any publicly known method such as coacervation, interfacial polymerization or an in-situ method, with no limitation to these. Since microcapsules containing a coloring agent and a developer, and their production methods, are known (for example, Japanese Unexamined Patent Publication No. 2007-132756 and Japanese Unexamined Patent Publication No. 2010-173087), the microcapsules confining a coloring agent to be used for the invention can be produced by omitting the developer in the production of such microcapsules.

Examples of film materials for capsules include publicly known substances such as urethane resins, melamine resins, urea resins, gelatin and gelatin-gum arabic, with no particular limitation to these, although urethane resins and melamine resins are preferably used.

The coloring agent microcapsules to be used for the invention may be of a single type or two or more types.

The concentration of the coloring agent in the microcapsules of the invention is preferably about 1 to 30 wt % and more preferably about 5 to 15 wt %, with no limitation to this range.

The coloring agent microcapsules may be used as a dispersion in a dispersing medium such as water at a solid concentration of about 1 to 60 wt %, preferably about 5 to 50 wt %, and more preferably about 10 to 30 wt %, but this is not limitative.

When the coloring agent microcapsules of the invention are subjected to pressure, heat and vibration (including ultrasonic waves), they are broken and release the coloring agent. Steps for applying pressure, heat and vibration (including ultrasonic waves) to base materials in methods for manufacturing absorbent articles are known. Specifically, embossing and ultrasonic treatment are carried out to apply pressure, vibration and/or heat, while laser working and heat embossing are carried out for heating. According to the invention, they may be steps for applying pressure, heat, vibration and ultrasonic waves that are publicly known for methods for manufacturing absorbent articles, or one or more from among pressure, heat, vibration and ultrasonic waves that are not known for methods for manufacturing absorbent articles but are carried out especially for the purpose of pattern formation. Since microcapsules that are broken by pressure, vibration or ultrasonic waves do not require heat as an essential condition, they allow coloring in a pattern that is not affected by the heat of a hot-melt adhesive joining step in the manufacturing process for the absorbent article, and they are therefore a preferred aspect, while not being limitative on the invention.

The conditions under which the coloring agent microcapsules are broken may be appropriately determined according to the type of base material of the absorbent article and the pattern that is to be formed. For example, when the coloring agent microcapsules are broken by embossing of the absorbent body, causing coloring in the embossing pattern, they preferably are broken at a pressure of 2.5 to 300 MPa or 10 to 180 MPa, and especially 50 to 150 MPa, which is used in embossing of absorbent bodies, although this is not limitative.

If the coloring agent microcapsules can be broken only under the pressure of embossing, then even if another heating step such as hot-melt joining, for example, is included, they will not be affected by the heating step and a coloring pattern can be formed solely by the action of the pressure and vibration of embossing. For this purpose, coloring agent microcapsules are used that are not broken at the heating temperature in hot-melt joining but are broken at the prescribed pressure of embossing. An example of a heating temperature employed for hot-melt joining is one in the range of 50 to 130° C. or in the range of 60 to 120° C., and particularly in the range of 70 to 100° C. (the heating temperature is the temperature when the hot-melt adhesive reaches the base material, and not the temperature of the hot-melt adhesive before applying or inside the nozzle). An example of pressure to be employed in hot-melt joining is one in the range of 0.01 to 50 MPa, and particularly in the range of 0.1 to 10 MPa. Therefore, it is sufficient to select coloring agent microcapsules that are not broken at the temperature and pressure actually employed in hot-melt joining, but are broken under the prescribed pressure and vibration of embossing.

Although one advantage of the invention is that the pattern formed in the second step can be free of the influence of other heating steps, this does not exclude heating during application of pressure or vibration in the second step. Ultrasonic vibration may also be used, and the conditions need only be sufficient for the coloring agent microcapsules to be broken.

Typically a heated roll will be used for heating in order to break the coloring agent microcapsules, and a temperature of, for example, 80 to 250° C. or 120 to 150° C. may be used, with no limitation to this range. A $CO_2$ laser, for example, may be used as a laser for breaking the coloring agent microcapsules, but this is not limitative.

The conditions for pressure, heat and vibration by which the coloring agent microcapsules of the invention are broken can be controlled by adjusting the material and dimensions of the microcapsules, or the thickness of the shells, and methods for manufacturing them are known to those skilled in the art.

For example, if the melting temperature or plasticizing temperature of the resin forming the capsules of the coloring agent microcapsules is designed to be higher than the heating temperature in the other heating steps, then the coloring agent microcapsules will not release the coloring agent at that heating temperature, and the coloring agent can therefore be released by pressure and vibration, avoiding the effect of the other heating steps.

(Coloring Agent)

According to the invention, the coloring agent is a substance (agent) that reacts with a developer to develop a color. It may be a simple compound or a mixture of compounds. The coloring agent to be confined in the microcapsules may be of a single color or multiple colors.

According to the invention, the coloring agent is preferably colorless before reacting with the developer. If the coloring agent is colorless, the manufacturing apparatus will not suffer color contamination even if the coloring agent adheres to it, and it will thereby be possible to prevent contamination of the product resulting from color contamination of the manufacturing apparatus.

The coloring agent used for the invention may be, for example, a known electron-donating coloring agent commonly used in pressure-sensitive paper and the like, and examples include, but are not limited to, blue coloring agents such as crystal violet lactone and 3,6-bis-diphenylaminofluorane, black coloring agents such as 2-anilino-3-methyl-6-N-methyl-pentylaminofluorane and 2-anilino-3-chloro-6-dimethylfluorane, red coloring agents such as 2-chloro-3-methyl-6-diethylaminofluorane and 1,2-benzo-6-diethylaminofluorane, and green coloring agents such as 2-dibenzylamino-6-diethylaminofluorane and 2-octylamino-6-diethylaminofluorane.

(Developer)

According to the invention, the developer is a substance (agent) that can react with a coloring agent (a coloring agent released from microcapsules) to develop a color. It may be a simple compound or a mixture of compounds. According to the invention, the coloring agent is preferably colorless, but when the coloring agent already has coloration, the developer is a substance (agent) that can develop a different color than that color.

Specifically, the developer of the invention may be, for example, a known electron-accepting developer that is commonly used for pressure-sensitive paper and the like, and examples include, but are not limited to, phenol resin-based compounds, salicylic acid-based metal chlorides, salicylic acid resin-based metal oxides and solid acid-based compounds.

The developer may be used as a dispersion in a dispersing medium such as water at a solid concentration of about 1 to 60 wt %, preferably about 5 to 50 wt %, and more preferably about 10 to 30 wt %, but this is not limitative.

(First Step: Application of Microcapsules to Base Material)

For the invention, the first step will usually be carried out before the second step. The first step may be carried out offline, instead of in a continuous process with the second step (online).

However, the first step and second step may also be carried out simultaneously. For example, the microcapsule applying solution may be applied onto the surface of a pressure roller such as an embossing roller (or optionally, only the surface of the pressing section), and while transferring the microcapsules from the surface of the pressure roller to the base material, the irregularities in the pressure roller may be simultaneously utilized to selectively press the base material and break the microcapsules in the prescribed pattern.

If the second step in which the microcapsules of the base material are broken in the desired pattern is preceded by a separate step in which the microcapsules can potentially be broken, such as a compacting step or joining step, then there is a risk of the microcapsules being broken in regions other than the desired pattern, and therefore such steps are preferably carried out before the first step. For example, if the process has a compacting step in which the core wrap (laminate) of the absorbent body is joined, then the first step of applying the microcapsules is preferably carried out after the compacting step, although there is no limitation to this order.

Also, instead of applying the microcapsules and developer onto the same surface of the base material, it is preferred for the microcapsules to be present on the back side of the surface of the base material on which the developer is applied, to allow the abrasion resistance of the microcapsules to be improved. Since manufacture of an absorbent article has steps involving contact with numerous manufacturing equipment parts, the base material has potential for direct contact between the manufacturing equipment and the microcapsules, but if the microcapsules are present on the back side of the base material then direct contact between the manufacturing equipment and microcapsules will not occur, and the risk of inadvertent breaking of the microcapsules will be reduced.

However, because of the steps of joining multiple structural members, when the first step is carried out after such joining steps it is difficult (although not impossible) to apply the microcapsules between the joined structural members, and therefore the microcapsules and the developer are usually applied onto the same surface as the joined structural members (the front side). For example, when the microcapsules are to be applied onto the core wrap of an absorbent body, in order to carry out the first step of applying the microcapsules after the compacting step of joining the core wrap, the microcapsules and developer are preferably applied onto the same surface of the core wrap, since the core wrap is already joined.

The method of applying the microcapsules on the base material may be a non-contact method such as spraying or ink-jet application, or a contact method using a coater or the like, and any common printing methods may be employed, with no particular limitation to these. It is preferred to use a non-contact method that has no potential for the microcapsules to be broken by contact.

In addition to applying, the microcapsules may also be included in the base material beforehand (especially the surface layer), during the manufacturing process for the base material.

The region in which the microcapsules are applied or supplied onto the base material may be the entire surface of the base material, or only a region that includes the pattern in which coloring is to be finally developed by the developer, or it may even be the same as the pattern to be colored. As an alternative to applying the entire surface of the base material, if the desired pattern is narrow, the applying may be only on part of the width of the base material, or the applying may be intermittent.

The type of coloring agent is not limited to a single color, but may be of multiple colors. One or more developers may be simultaneously or separately applied onto a multicolor coloring agent, developing the multiple colors either simultaneously or sequentially.

When a plurality types of coloring agent microcapsules are to be applied onto the base material, the plurality types of coloring agent microcapsules may be simultaneously or sequentially applied in the first step before carrying out the second step and third step, or after applying a certain type of coloring agent microcapsules on the base material in the first step and carrying out the second step and third step, the first step may be carried out again to apply another type of coloring agent microcapsules onto the base material, and then the second step and third step repeated. If such a method of applying multiple types of coloring agent microcapsules is utilized, then when the base material is a laminate or a composite member, the same or different types of coloring agent microcapsules may be applied onto a different structural member that is the same or different from the laminate or composite member, and their colors produced.

When microcapsules are applied onto a base material, they may be applied onto either of the two surfaces of the base material (the upper surface side on which the developer is applied or the lower surface side which is the opposite side), but it is often difficult to accomplish applying on the opposite side from the front side on which the developer is applied, depending on the manufacturing process.

When microcapsules are to be applied onto a base material, the basis weight of the microcapsules is preferably in the range of 0.1 to 15 gsm or even 0.5 to 5 gsm (where "gsm" stands for $g/m^2$), although this is not limitative. At less than 0.1 gsm, it may not be possible to obtain adequate coloring even if the concentration of the coloring agent in the microcapsules has been increased within the allowable range. At greater than 15 gsm, excess water will be applied to the absorbent body, potentially leading to increased hardness of the absorbent body and a reduced absorption property.

According to the invention, since only the coloring agent microcapsules are applied in the first step, without applying the developer, it is possible to reduce the amount of water in the applying solution used in the first step, compared to Patent Literature 1 wherein the coloring agent microcapsules and the developer are simultaneously applied in the first step. While the amount of water can be reduced by increasing the concentration of the coloring agent microcapsules or developer in the applying solution, this is not always a desirable situation for applying, and there is also a limit to this strategy. When the base material is an absorbent body or the like, and the base material contains a large amount of water, there is a risk of problems occurring during the process of applying pressure, vibration or heat using a pattern roll or the like in the second step, such problems including hardening of the base material or wrapping around the pattern roll, but according to the invention this risk can be reduced. When the base material is an absorbent core comprising pulp and a superabsorbent polymer, applying of water onto the base material before embossing may be avoided, or if water is applied, it is preferably applied with a water content of no greater than 5 wt % or in the range of 1.5 to 4.5 wt % based on the weight of the absorbent core, although this is not limitative.

(Second Step: Breaking of Microcapsules)

According to the invention, the second step of breaking the microcapsules is carried out before the third step of applying the developer. By carrying out the second step and the third step separately, the pattern of the coloring agent and the pattern of the coloring can be separately controlled, and by using a colorless coloring agent it is possible to prevent coloring contamination of the manufacturing apparatus used for breaking of the microcapsules.

The method for breaking the microcapsules applied or supplied onto the base material to release the coloring agent in the prescribed pattern in the base material need only be a method that allows the microcapsules to be broken in the prescribed pattern, and for example, pressure, heat, vibration, ultrasonic waves or the like may be used. Pressure, vibration and ultrasonic waves are preferred methods, but heating may also be combined with them. Ultrasonic waves may also include vibration.

For example, if the method uses pressure-sensitive microcapsules and pressure and/or vibration is applied that is at least sufficient for breaking of the pressure-sensitive microcapsules, then the method does not utilize a coloring property by heating as described for Patent Literature 1, and is therefore preferred as it will allow coloring in only the specific pattern by embossing.

Particularly when the microcapsules are broken by (the pressure or vibration of) embossing which is commonly used with absorbent articles, a pattern can be colored by the embossing, which is preferred from the viewpoint of process control, and also from the viewpoint of utilizability of the product such as the sense of quality and apparent aesthetic property perceived by the user of the absorbent article. In particular, compression grooves extending in the depthwise direction from the upper wrap sheet to the absorbent core and lower wrap sheet, in a double linear pattern extending in the long direction along both edges in the short direction of the absorbent body (which may include the skin side sheet placed over the absorbent body, and also the non-skin side sheet), act as folding line origins (guide lines) for the absorbent body, and therefore coloration and high visibility of the pattern of squeeze grooves (hinges) is effective for imparting a high-quality, positive feel for the user.

In addition, embossing in a lattice-like or dotted form is sometimes formed at the center section of the absorbent body in order to modify the density of the absorbent core, and coloration and high visibility of such an embossing pattern is effective for imparting a high-quality, positive feel for the user.

When microperforations are provided in the outer section around the waist of the disposable diaper to provide and create air permeability, coloring the pattern of the microperforations blue, for example, can elicit a sense of air permeability. The microcapsules may be broken in the step of forming the microperforations, allowing the pattern of microperforations (their surrounding walls) to be colored.

In manufacture of an absorbent article which comprises multiple structural members, it is common to employ a hot-melt joining step in which hot-melt joining is carried out between the multiple structural members. In such cases, if it is desired to break the microcapsules and form a coloring pattern by pressure, vibration and/or ultrasonic waves (especially in an embossing step) in a pattern different from the hot-melt joining step, then if a hot-melt joining step is carried out in addition to the step of applying the pressure, vibration and/or ultrasonic waves (especially in an embossing step) as the second step after the step of supplying the microcapsules to the base material, the coloring agent microcapsules used are preferably ones that are broken by the pressure, vibration and ultrasonic waves of the second step but are not broken at the heating temperature (and pressure) of the hot-melt joining step, since they will not be affected by heating in the hot-melt joining step and it will be possible to develop the color in the pattern only during the step of applying the pressure, vibration and/or ultrasonic waves in the second step (especially an embossing step).

In a pressing step such as embossing, vibration is sometimes also utilized in addition to pressure, allowing the microcapsules to be broken by this vibrational energy.

(Third Step: Application of Developer, Color Development)

According to the invention, the third step of applying the developer is carried out after the second step of breaking the microcapsules.

If a developer is applied after the microcapsules have been broken to release the coloring agent into the base material in the prescribed pattern, the developer is reacted with the coloring agent to develop the color of the coloring agent released in the prescribed pattern.

The method of applying the developer is not particularly restricted so long as it allows applying, and it may be a non-contact method such as spraying or ink-jet application, or a contact method using a coater or the like, while any common printing methods may also be employed, with no particular limitation to such methods. It is preferred to use a non-contact method that has no potential for the microcapsules to be broken by contact.

The developer is applied so as to overlap with at least a portion and preferably all of the prescribed pattern in which the coloring agent has been released, with the color being developed in the prescribed pattern in the overlapping regions. That is, applying of the developer may be over the entire surface of the base material, but if the desired pattern is narrow, the applying may be on part of the width of the base material or, intermittent.

Applying of the developer is preferably carried out on the same surface as the front side of the base material on which the coloring agent has been applied, but it may instead be applied on the surface on the opposite side from the front side on which the coloring agent has been applied.

Since the step of applying the developer is after the second step in which pressure and ultrasonic waves are applied, the water content during applying the developer has little effect even if the base material is an absorbent body, unlike the water content in the first step.

(Example of Application to Absorbent Body)

According to one embodiment of the invention, the method of forming a coloring pattern in an absorbent body by embossing may comprise laminating a skin side wrap sheet (upper tissue), an absorbent core (ground pulp and superabsorbent polymer) and a non-skin side wrap sheet (lower tissue), pressing the obtained laminate to form a laminate of approximately constant thickness, subsequently applying coloring agent microcapsules onto the skin side of the skin side wrap sheet, and then carrying out a step of pressing (embossing) the laminate to break the coloring agent microcapsules in the prescribed pattern and apply the developer, to thereby develop the color. The obtained laminate is cut to a prescribed shape to produce an absorbent body.

FIG. 1 shows an overview of the manufacturing process for an absorbent body according to an example of the invention, the flow of the process and materials being from right to left in FIG. 1. In FIG. 1, the top side in the figure is the skin side.

A hot-melt adhesive (HMA) 4 is applied onto the skin side of the lower tissue 1, and in the following step an absorbent core 3 containing ground pulp and a superabsorbent polymer is laminated in an essentially uniform manner from above the lower tissue 1. After an HMA 5 has been applied onto the non-skin side of the upper tissue 2, the upper tissue 2 is merged with the absorbent core 3 to obtain a laminate 10-0.

In the subsequent step, a pair of flat press rolls 6 are used to press the laminate 10-0 to an approximately constant thickness, to form a laminate 10-1.

The coloring agent microcapsule dispersion is applied onto the skin side (embossing side) of the laminate 10-1 in such an amount to have a prescribed basis weight using a spray apparatus 7, and a laminate 10-2 is formed.

For this example, the applying surfaces of the coloring agent in the first step and the developer in the third step are the same (the skin side of the upper tissue 2), but if the coloring agent in the first step is applied onto the non-skin side of the upper tissue 2, and therefore different from the applying surface of the developer in the third step (the skin side of the upper tissue 2), then a design with strong abrasion resistance (to avoid unexpected coloration) can be obtained. In this case, however, it is necessary to adjust the specifications of the capsules or the conditions of the press rolls so that the capsules are not broken by the press rolls 6.

The laminate 10-2 that is conveyed beyond the spray apparatus 7 is then passed through embossing rolls (a first embossing roll 8-1 and second embossing roll 8-2) to form embossing (recesses) in the laminate 10-2, and the microcapsules are broken at the embossed sections to produce a laminate 10-3.

Figure 2:
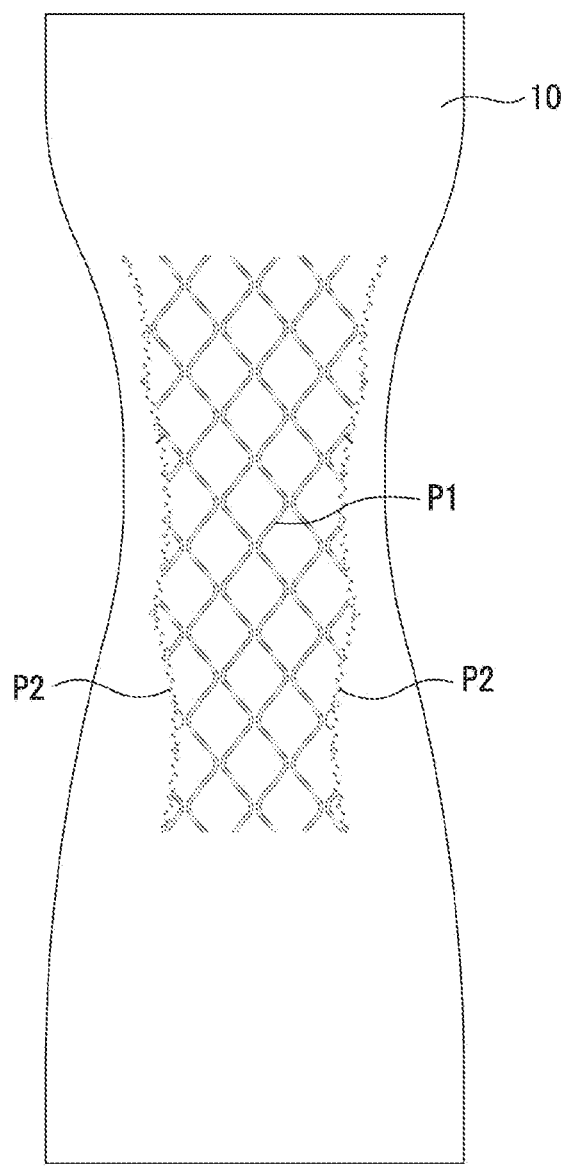
FIG. 2 is a diagram showing an example of a coloring pattern in an absorbent body produced by the manufacturing process of FIG. 1.

On the skin side (embossing side) of the laminate 10-3 in which the coloring agent microcapsules have been partially broken by the first embossing roll 8-1 and second embossing roll 8-2, a developer dispersion is applied in such an amount to have a prescribed basis weight using the spray apparatus 9, and reaction is carried out with the coloring agent to obtain a laminate 10-4 colored in the pattern of the embossing (for example, lattice-like embossing P1 and embossing P2 to serve as flexion base points, in FIG. 2). Incidentally, in the laminate 10-4, coloration is not seen in the regions in which the hot-melt adhesive has been applied and the regions that have been pressed with the press rolls. The laminate 10-4 is then cut to a prescribed shape to produce an absorbent body.

The embossing of the laminate by the manufacturing method described above is not restricted, and for example, an absorbent body obtained as the final product by a process that comprises the aforementioned steps may comprise the lattice-like embossing (recesses) at the center section of the absorbent body, formed by a first embossing roll, and the flexion base point embossing (recesses) along the MD direction of the absorbent body, formed by a second embossing roll. As an absorbent body 10 obtained as the final product from the laminate formed using the combination of the first embossing roll and second embossing roll in this manner, FIG. 2 shows the lattice-like embossing P1 at the center section formed by the first embossing roll and the embossing P2 to serve as flexion base points extending along the MD direction of the absorbent body MD, formed by the second embossing roll. The embossing P2 to serve as flexion base points consists of squeeze grooves (hinges) that are to serve as flexion base points for folding of the absorbent body in the short direction (widthwise direction), and it reaches from the upper tissue 1 through the absorbent core 3 to the lower tissue 2.

(Example of Other Embodiment of Absorbent Body)

A modified example of an embodiment of the method of forming the coloring pattern by embossing in the absorbent body manufacturing process, may comprise applying the coloring agent microcapsules onto the non-skin side of the skin side wrap sheet (upper tissue), followed by laminating the skin side wrap sheet with the absorbent core and non-skin side wrap sheet (lower tissue), pressing the laminate to form a laminate of approximately constant thickness, then pressing (embossing) the laminate to break the coloring agent microcapsules in a prescribed pattern, and applying a developer to develop the color. The laminate may then be cut to a prescribed shape to produce an absorbent body.

Figure 3:
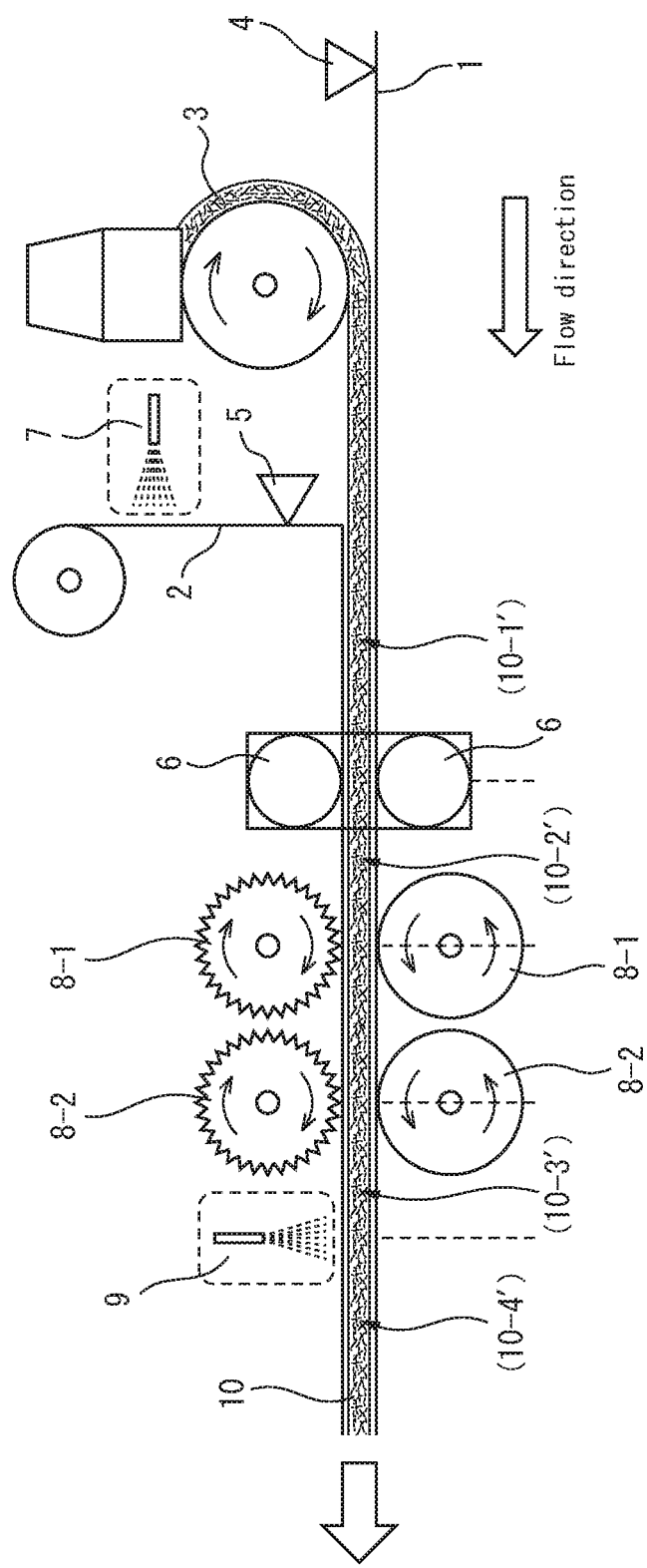
FIG. 3 is a diagram showing another example of a manufacturing process for an absorbent body of the invention.

An example of another embodiment of such an absorbent body manufacturing process is illustrated in FIG. 3.

The manufacturing process shown in FIG. 3 is similar to the absorbent body manufacturing process described using FIG. 1, and therefore explanation of the same steps will be omitted and the same reference numerals will be used.

In FIG. 3, the manufacturing process is the same as in FIG. 1, except that a hot-melt adhesive (HMA) 4 is applied onto the skin side of the lower tissue 1, in the subsequent step the absorbent core 3 is laminated in an essentially uniform manner from above the lower tissue 1, an HMA 5 is applied onto the non-skin side of the upper tissue 2, after which it is merged onto the absorbent core 3, and in the following step, a pair of flat press rolls 6 are used to press the laminate to an approximately constant thickness.

In FIG. 3, however, before applying the HMA 5 on the non-skin side of the upper tissue 2, the coloring agent microcapsule dispersion is applied on the same non-skin side as the upper tissue 2 (the back side of the embossed side) in such an amount to have a prescribed basis weight using the spray apparatus 7. The upper tissue 2 on which the coloring agent microcapsule dispersion has been applied and the HMA 5 has been further applied is merged onto the absorbent core 3 to obtain a laminate 10-1'. The laminate 10-1' is pressed using the pair of flat press rolls 6 in the subsequent step, to form a laminate 10-2'. The laminate 10-2' at this stage is the same as the laminate 10-2 shown in FIG. 1, except for having the coloring agent microcapsule dispersion applied onto the non-skin side of the upper tissue 2.

The laminate 10-2' is then pressed into the prescribed pattern by the first embossing roll 8-1 and second embossing roll 8-2, similar to the step illustrated in FIG. 1, to form a laminate 10-3' with embossing (lattice-like embossing P1 and embossing P2 to serve as flexion base points, in FIG. 2), formed in it. Next, the laminate 10-3' is applied with the developer using the spray apparatus 9, to obtain a laminate 10-4' with color developed in the pattern of the embossing (the lattice-like embossing P1 and the embossing P2 to serve as flexion base points, in FIG. 2). The laminate 10-4' is then cut to the prescribed shape to form an absorbent body.

In the manufacturing process shown in FIG. 3, the coloring agent microcapsule dispersion is applied on the non-skin side of the upper tissue 2, or in other words on the back side from the surface on the side of embossing and applying of the developer. Since the coloring agent microcapsules are on the non-front side of the base material (the upper tissue in this case) and are not directly exposed to the outside, unexpected coloring caused by applying of the developer is minimized, and since the coloring agent microcapsules are protected by the base material in each of the subsequent working steps of the manufacturing process for the product, an effect of improved abrasion resistance is obtained.

Moreover, with this embodiment, applying of the coloring agent microcapsules onto the upper tissue (base material) is followed by the steps of applying a hot-melt adhesive and pressing with the press rolls 6, but no coloring appears in the regions applied with the hot-melt adhesive or the regions pressed with the press rolls 6, even after the developer has been applied. It is possible to obtain coloring only in the pattern of embossing formed by the first embossing roll 8-1 and second embossing roll 8-2. This is because the coloring agent microcapsules are not broken at the applying temperature of the hot-melt adhesive or the pressure of the press rolls 6, the coloring agent microcapsules only being broken by pressure above the prescribed level, by the first embossing roll 8-1 and second embossing roll 8-2.

For this embodiment the coloring was effected in the upper tissue (base material) of the absorbent body, but according to the invention the coloring may be effected in the lower tissue (base material) of the absorbent body either in the same steps as this embodiment, or with additional steps either before or after the coloration step of this embodiment.

(Example of Disposable Diaper)

Figure 4:
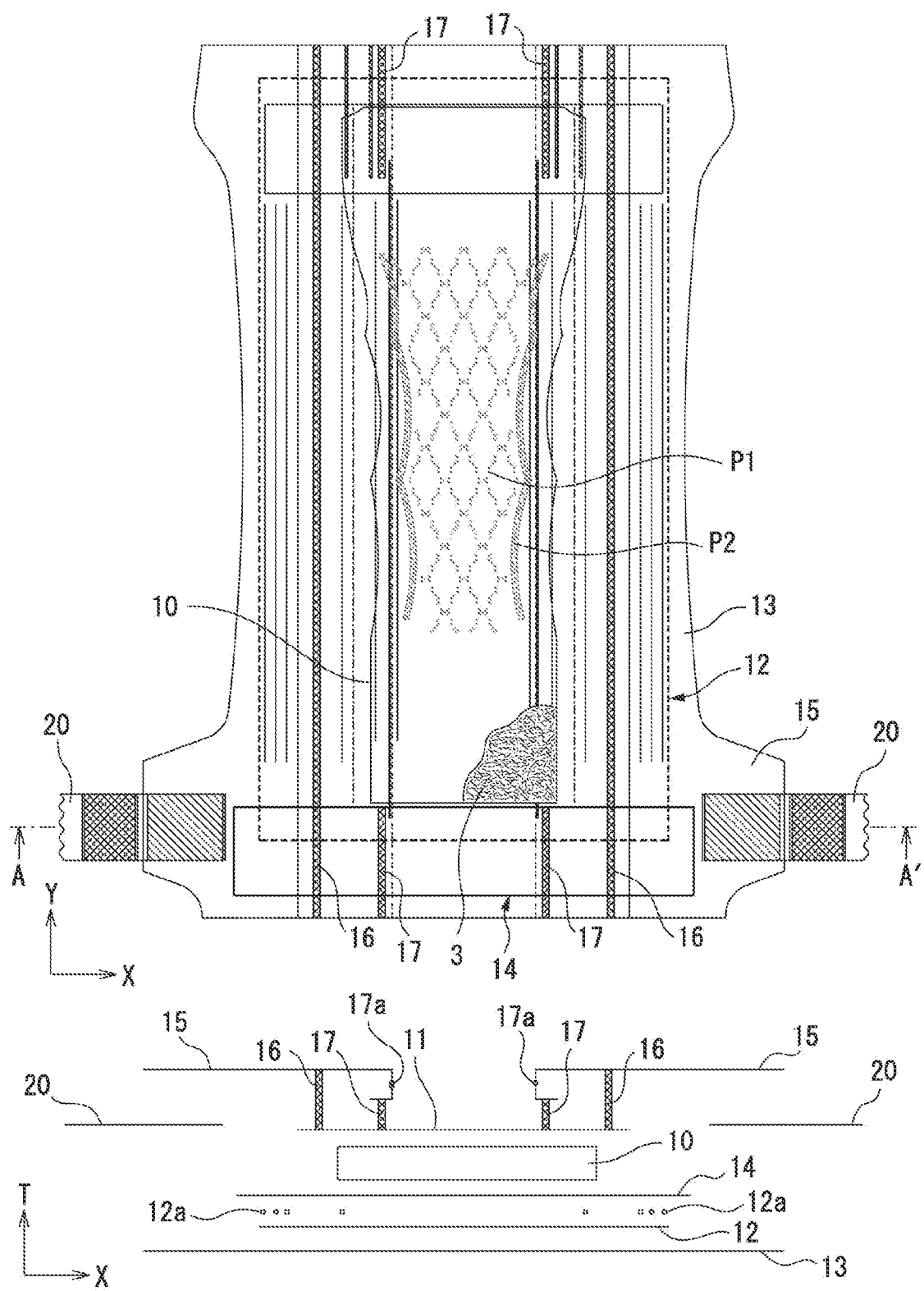
FIG. 4 is an expanded plan view of an example of a tape-type disposable diaper, and a schematic cross-sectional view shown cut on line A-A' of the expanded plan view.

FIG. 4 shows an expanded plan view (top) and a cross-sectional view of the top diagram cut on line A-A (bottom), of an example of a tape-type disposable diaper produced through additional assembly steps, using an absorbent body produced by the manufacturing process described above with reference to FIGS. 1 to 3. However, for the absorbent body 10 shown in the example of the disposable diaper in FIG. 4, while the shape of the absorbent body 10 and the patterns of the embossings P1, P2 do not completely match those shown in FIG. 2, they are essentially the same.

The disposable diaper has a long direction Y and a short direction X, as shown in the plan view at the top of FIG. 4, and a short direction X and a thickness direction T, as shown in the schematic cross-sectional view at the bottom of FIG. 4.

The absorbent body 10 is located at the center section in the long direction Y and short direction X of the disposable diaper, and has a liquid-permeable top sheet 11 on the skin side of the absorbent body 10 (the front end direction perpendicular to the plane of the plan view at the top of FIG. 4 and the upper direction in the plane of the schematic cross-sectional view at the bottom of FIG. 4) and a liquid-impermeable back sheet 12 and back nonwoven fabric 13 on the opposite side from the skin side (the non-skin side). The wrap film of the absorbent body 10 is bonded to the back sheet 12, for example, and held in the diaper.

In FIG. 4, the absorbent body 10 is shown partially broken, the absorbent core 3 being visible in the broken portion.

The top sheet 11, back sheet 12 and back nonwoven fabric 13 are larger than the absorbent body 10 and determine the general outer shape of the diaper, but at the outer periphery of the absorbent body 10 there are formed a waist flap around the waist and leg flaps around the legs.

In addition, it has a waist gather film 14 extending in the girth direction along both edges in the long direction Y of the diaper, the waist gather film 14 being made of an elastic material, and contracting in the direction around the girth direction to form a waist gather together with the top sheet 11 and back sheet 12.

Elastic solids 12a are joined at the portions of the top sheet 11, back sheet 12 and back nonwoven fabric 13 that are to surround the legs, thereby forming leg gathers.

On the skin side of the top sheet 11 there is provided a leg standing gather nonwoven fabric 15, extending in the long direction, shifted slightly toward the center from both edges in the short direction X. The leg standing gather nonwoven fabric 15 is joined to the top sheet 11 by joining means 16 in the long direction near both edges in the short direction, and is folded to the center direction in the short direction X, while elastic members 17a are joined at the edges in the center direction in the folded short direction X, and joined to the top sheet 11 by joining means 17, at the portions of the edges in the center direction in the folded short direction X and near both edges thereof in the long direction Y. As a result, when the diaper is being worn, the leg standing gather nonwoven fabric 15 is folded toward the center section in the short direction X and stands up from the top sheet 11, forming leg standing gathers. The leg standing gather nonwoven fabric 15 extends across almost the entire length of the diaper, forming attachment extensions 15' of the fitting tape 20 at the edges on the abdomen side in the long direction Y. and extends to both side sections of the back nonwoven fabric 13 at the center section in the long direction Y, forming flaps around the legs, the elastic solids 12a being joined to form gathers around the legs.

Fitting tape 20 is also attached at both side sections in the short direction X of the edges on the back side in the long direction Y of the diaper, as anchoring means during fitting of the tape-type diaper.

In manufacture of such a disposable diaper, after the absorbent body described with reference to FIGS. 1 to 3 has been produced, hot-melt joining is relatively frequently carried out during the course of assembling the disposable diaper. For example, the top sheet 11 may be hot-melt joined to the absorbent body 10. In such cases, in the method for manufacturing an absorbent body described with reference to FIGS. 1 to 3, wherein the coloring pattern is formed by the pressure of embossing rolls, it is possible to prevent formation of an undesired coloring pattern on the absorbent body even if it is followed by a hot-melt joining step. However, it should be noted that the present invention is not limited to this type of embodiment.

The invention has been described above based on an example of selectively coloring embossing (shaping) in the absorbent body of a tape-type diaper, but the invention is not limited to this example, and needless to mention, it can also be applied to other embossing patterns of absorbent bodies, patterns other than embossing, base materials other than diapers, and absorbent articles other than diapers, such as sanitary napkins and incontinence pads. For example, the absorbent body described with reference to FIGS. 1 to 4 can also be applied to an absorbent article other than a diaper, such as a sanitary napkin or incontinence pad.

(Example of Application to Outer Section Around the Waist)

Figure 5:
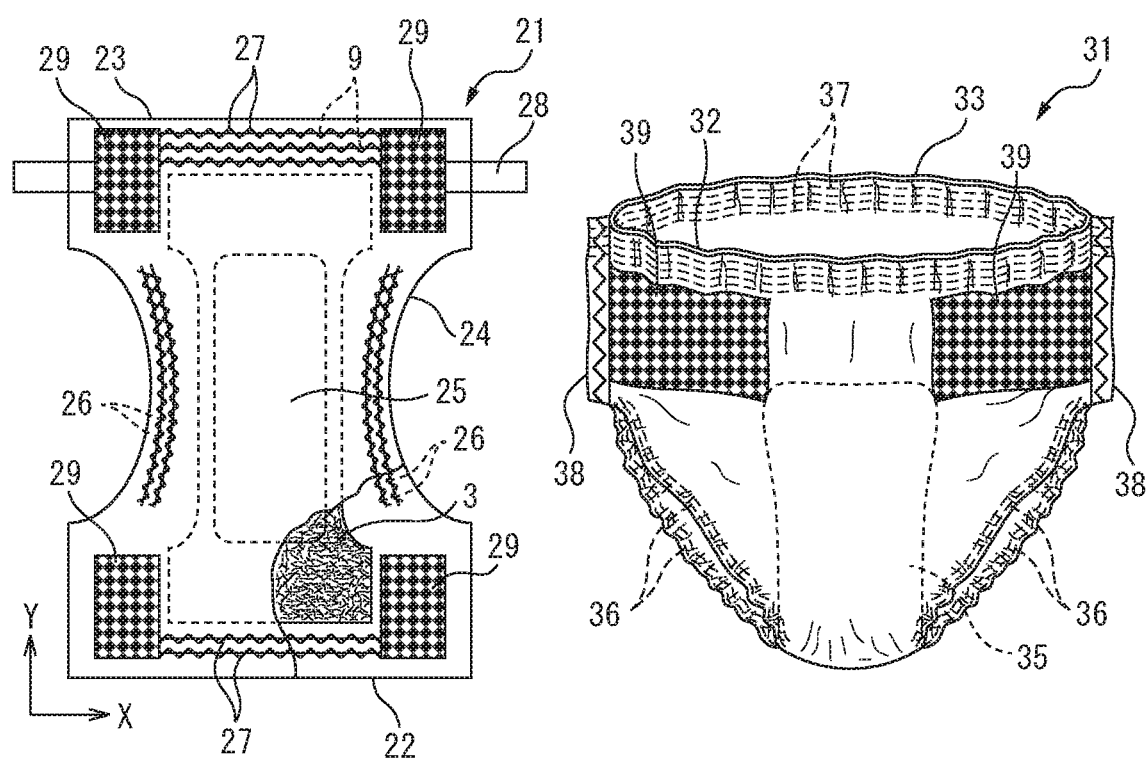
FIG. 5 is a diagram illustrating an example of the invention being applied to an aeration hole of the outer section around the waist.

FIG. 5 shows an example of the invention being applied to aeration holes in the outer section around the waist.

FIG. 5 is an example of a tape-type diaper and pants-type diaper, wherein air permeability is improved by providing microperforations in the outer section around the waist (the surface visible on the outside). When microperforations are provided in the outer section around the waist, a coloring method may be employed that uses the coloring agent microcapsules of the invention for blue coloration of a pattern of microperforations, to obtain an effect that creates a sense of air permeability.

The diapers of FIG. 5 are similar to a conventionally known tape-type diaper and pants-type diaper, except that they have microperforations formed in the outer section around the waist, and apply the present invention to form blue color in the pattern of microperforations.

For FIG. 5, therefore, only the reference numerals are assigned and the names will be mentioned, while the detailed description of the construction and method of manufacturing will be omitted. A tape-type diaper 21 is shown at left in FIG. 5, having a long direction Y and a short direction X. Reference numeral 22 is the edge on the abdomen side in the long direction Y (flap), 23 is the edge on the back side in the long direction Y (flap), 24 are the edges around the legs, (flaps), 25 is the absorbent body, 26 are elastic solids around the legs, 27 are elastic solids around the waist, 28 is a fitting tape, and 29 are regions where the microperforations are formed in the outer section around the waist. At left in FIG. 5, the absorbent body 25 is shown partially torn, an absorbent core 3 being visible inside the torn portion. The microperforations in the outer section around the waist are colored blue in the pattern, as a construction whereby a sense of air permeability is created.

A pants-type diaper 31 is shown at right in FIG. 5, wherein 32 is the abdomen side flap around the waist, 33 is the back side flap around the waist, 34 are flaps around the legs, 35 is the absorbent body, 36 are elastic solids around the legs, 37 is elastic solids around the waist, 38 are joining sections, and 39 are regions where the microperforations are formed in the outer section around the waist. The microperforations in the outer section around the waist are colored blue in the pattern, as a construction whereby a sense of air permeability is created.

In the tape-type diaper and pants-type diaper shown in FIG. 5, the method of coloration in the pattern of microperforations may be a method of providing a step of applying the coloring agent microcapsules onto the top sheet before the step of forming the microperforations, when a step of forming microperforations in the diaper is to be carried out, and then comprising a step of forming the microperforations by embossing, for example, to break the coloring agent microcapsules and release the coloring agent in the pattern of the microperforations, and subsequently applying the developer and causing coloration of the coloring agent released in the pattern of the microperforations. When the microperforations are formed by embossing, the coloring agent microcapsules are broken at the locations of the microperforations, and the coloring agent is released onto the wall faces forming the microperforations, to allow coloration in the pattern of the microperforations.

EXAMPLES

An example of a manufacturing process for an absorbent body to be used in an absorbent article will now be described with reference to the attached drawings.

Referring to the process drawing of FIG. 1, the skin side of a lower tissue (basis weight: 16 g/m$^2$) 1 (the upper side in FIG. 1) is applied with a hot-melt adhesive (HMA) (basis weight: 10 g/m$^2$) 4 (the temperature of the HMA upon reaching the base material was 80° C.), and in the following step, an absorbent core 3 which was a mixture of ground pulp (basis weight: 270 g/m$^2$) and a superabsorbent polymer (basis weight: 215 g/m$^2$) was laminated in an essentially uniform manner on the lower tissue 1. After applying an HMA (basis weight: 10 g/m$^2$) 5 onto the non-skin side of an upper tissue (basis weight: 16 g/m$^2$) 2 (the lower side in FIG. 1) (the temperature of the HMA upon reaching the base material was 80° C.), it was merged onto the absorbent core 3, to form a laminate 10-0 of the lower tissue 1, the absorbent core 3 and the upper tissue 2.

In the subsequent step, a pair of flat press rolls (80° C., 10 MPa) 6 were used to press the laminate 10-0 to a thickness of approximately 2.5 mm, to form a laminate 10-1.

The coloring agent microcapsule dispersion (solid content: 10 wt %) was applied onto the skin side (embossing side) of the laminate 10-1 in such an amount to be a basis weight of 15 g/m$^2$ using a spray apparatus 7, to form a laminate 10-2.

The coloring agent microcapsule dispersion was prepared as a coloring agent microcapsule dispersion containing coloring agent microcapsules comprising crystal violet lactone covered with a urethane resin film, at a solid content of 10 wt %.

The laminate 10-2 that was conveyed beyond the spray apparatus 7 was then embossed by a first embossing roll (85° C., 70 MPa) 8-1, while breaking the microcapsules in the embossed sections. The embossing that was formed was the lattice-like embossing P1 at the center section of the finally produced absorbent body, as shown in FIG. 2.

The laminate 10-2 was then embossed with a second embossing roll (100° C., 100 MPa) 8-2, while breaking the microcapsules in the embossed sections, to form laminate 10-3. The embossing that was formed was the embossing P2 to serve as flexion base points along the MD direction of the final absorbent body product, as shown in FIG. 2.

On the skin side (embossing side) of the laminate 10-3 in which the coloring agent microcapsules were broken in the prescribed pattern by the first embossing roll 8-1 and second embossing roll 8-2, a developer dispersion (solid content: 10 wt %) was applied in an amount to be a basis weight of 15 g/m$^2$ using the spray apparatus 9, and reaction was carried out with the coloring agent to obtain a laminate 10-4 wherein the embossed sections (embossing formed by the first embossing roll 8-1 and second embossing roll 8-2) were colored sky-blue (light blue). However, there was no coloration in the laminate 10-4 in the regions applied with the hot-melt adhesive or the regions pressed by the press rolls 6.

The developer dispersion was prepared using zinc 3,5-di (α-methylbenzyl)salicylate as the developer, with the developer at a solid content of 10 wt %.

Crystal violet lactone forms a blue color upon reacting with the developer and undergoing the following chemical change.

[Chemical Formula 1]

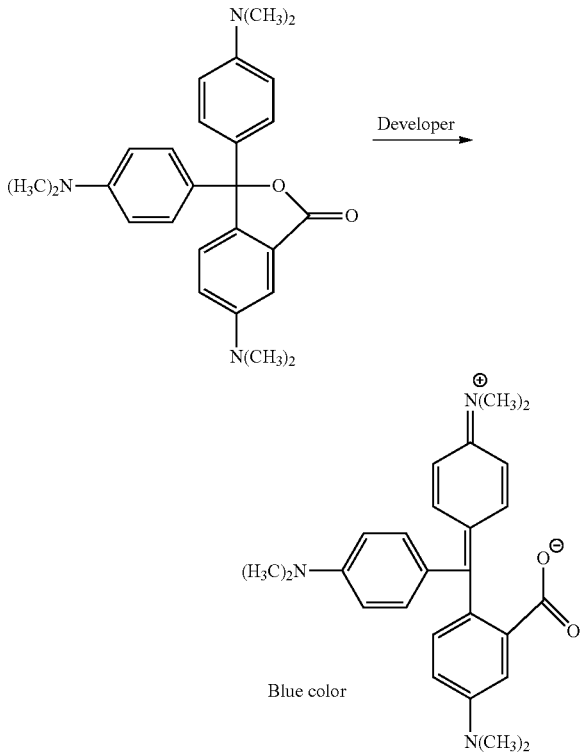

The final absorbent body obtained from the laminate 10-4 produced by the steps described above was colored sky-blue (light blue) in the sharp pattern of embossing, in both the lattice-like embossing P1 at the center section of the absorbent body and the embossing P2 to serve as flexion base points along the MD direction of the absorbent body MD, and the product had excellent visibility of the prescribed pattern of the embossing, while also presenting a feeling of cleanliness due to the light blue coloration, and exhibiting a high quality feel compared to an equivalent conventional product without coloring.

As a comparative example, the example described above was modified in the following aspects. Specifically, the coloring agent microcapsules, as pressure-sensitive microcapsules, and the developer were both used in the first step, the color was developed in the pattern of embossing by embossing rolls in the second step, and the third step was omitted. The solid concentrations of the coloring agent microcapsules and the developer were both 5 wt %, and the applying amounts in the first step in which the coloring agent microcapsules and developer were applied were 30 gsm (water content: 27.0 gsm). As a result, the water content in the laminate during embossing for the comparative example was twice as great as the water content of 13.5 gsm in the first step of the example, and problems occurred such as hardening of the laminate for formation of the absorbent body during embossing, and wrapping of the laminate onto the embossing roll.

INDUSTRIAL APPLICABILITY

The method for manufacturing an absorbent article of the invention is useful for manufacture of absorbent articles such as disposable diapers, sanitary napkins and incontinence pads.

REFERENCE SIGNS LIST

1 Lower tissue
2 Upper tissue
3 Absorbent core
4, 5 Hot-melt adhesive
6 Press roll
7 Spray apparatus
8-1 First embossing roll
8-2 Second embossing roll
9 Spray apparatus
10 Absorbent body
P1 Lattice-like embossing
P2 Embossing for flexion base points
21 Tape-type diaper
29 Microperforation region
31 Pants-type diaper
39 Microperforation region

The invention claimed is:

1. A method for manufacturing an absorbent article having a base material, the method comprising
a first step for providing a base material having microcapsules confining a coloring agent,
a second step for breaking the microcapsules in a prescribed pattern in the base material to release the coloring agent into the base material in the prescribed pattern, and
a third step for applying a developer onto the base material in which the coloring agent has been released in the prescribed pattern, to react and the coloring agent and the developer to thereby effect coloring in at least a portion of the prescribed pattern.

2. The method according to claim 1, wherein in the second step, the microcapsules are broken by applying at least one selected from among pressure, heat and vibration.

3. The method according to claim 1, wherein in the second step, the microcapsules are broken in the prescribed pattern by embossing, and in the third step, the coloring is effected in at least a portion of the prescribed pattern.

4. The method according to claim 1, wherein the base material comprises an absorbent body.

5. The method according to claim 4, wherein the absorbent body comprises an absorbent core between an upper wrap sheet and a lower wrap sheet, and in the first step, the microcapsules are supplied to the upper wrap sheet and/or and the lower wrap sheet, while in the third step, the coloring is effected in the upper wrap sheet and/or the lower wrap sheet.

6. The method according to claim 5, wherein in the first step the microcapsules are supplied to the upper wrap sheet, in the second step squeeze grooves are formed in the absorbent body extending in the depthwise direction from the upper wrap sheet to the absorbent core and the lower wrap sheet, and in the third step the coloring is effected as a pattern of the squeeze grooves in the upper wrap sheet.

7. The method according to claim 4, wherein the absorbent article has a multilayer structure additionally comprising a skin side sheet on the skin side of the absorbent body and/or a non-skin side sheet on the non-skin side, in the first step the microcapsules are supplied to the absorbent body, the skin side sheet and/or the non-skin side sheet, and in the third step the coloring is effected in the absorbent body, the skin side sheet and/or the non-skin side sheet.

8. The method according to claim 1, wherein the absorbent article is a disposable diaper, and a plurality of microperforations are formed on the outer section around the waist of the disposable diaper, the pattern of the microperforations being colored in the third step.

9. The method according to claim 1, wherein the surface of the base material having the microcapsules is the surface on the same side as the side of the base material on which the developer is applied.

10. The method according to claim 1, wherein the surface of the base material having the microcapsules is the surface on the opposite side from the side of the base material on which the developer is applied.

11. The method according to claim 1, which further comprises a hot-melt joining step in which the base material is hot-melt joined to another structural member, and the first step is carried out after the hot-melt joining step.

12. The method according to claim 1, which further comprises a hot-melt joining step in which the base material is hot-melt joined to another structural member, the hot-melt joining step being after the first step but without breaking of the microcapsules in the hot-melt joining step.

* * * * *